(12) United States Patent
Hand et al.

(10) Patent No.: US 6,499,160 B2
(45) Date of Patent: Dec. 31, 2002

(54) HOSPITAL BED

(75) Inventors: Barry D. Hand, Mt. Pleasant, SC (US); Dana H. Delk, North Charleston, SC (US); Jack J. Brooks, Folly Beach, SC (US); Steven J. Doehler, Charleston, SC (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 09/944,558

(22) Filed: Aug. 31, 2001

(65) Prior Publication Data

US 2002/0026671 A1 Mar. 7, 2002

Related U.S. Application Data

(63) Continuation of application No. 09/499,200, filed on Feb. 7, 2000, now Pat. No. 6,282,736, which is a continuation of application No. PCT/US98/16497, filed on Aug. 7, 1998.
(60) Provisional application No. 60/055,043, filed on Aug. 8, 1997, and provisional application No. 60/090,212, filed on Jun. 22, 1998.

(51) Int. Cl.[7] .............................................. A61G 13/04
(52) U.S. Cl. ................................ 5/608; 5/607; 5/600
(58) Field of Search ........................... 5/600, 601, 607, 5/608, 609, 610, 611, 629

(56) References Cited

U.S. PATENT DOCUMENTS

| | | | | |
|---|---|---|---|---|
| 1,021,335 A | * | 3/1912 | Robinson | 5/607 |
| 1,573,571 A | | 2/1926 | Pohl | 378/179 |
| 1,667,982 A | | 5/1928 | Pearson | 5/608 |
| 1,799,692 A | | 4/1931 | Knott | 5/607 |
| 2,076,675 A | | 4/1937 | Sharp | 5/609 |
| 2,239,821 A | | 4/1941 | Knox | 5/607 |
| 2,311,542 A | | 2/1943 | Holme | 5/609 |
| 2,499,101 A | | 2/1950 | Kluglein | 5/607 |
| 2,607,103 A | | 8/1952 | Davidson | 27/28 |
| 2,613,371 A | | 10/1952 | Keyes, Jr. | 5/607 |
| 2,639,206 A | | 5/1953 | Butler | 5/621 |
| 2,667,169 A | | 1/1954 | Kambourakis | 607/95 |
| 2,673,987 A | | 4/1954 | Upshaw et al. | 5/86.1 |
| 2,880,720 A | | 4/1959 | Houghtaling | 601/90 |
| 2,902,701 A | | 9/1959 | Driskill | 5/607 |
| 3,049,726 A | | 8/1962 | Getz | 5/86.1 |
| 3,110,912 A | | 11/1963 | Propst | 5/628 |
| 3,200,416 A | | 8/1965 | Warrick | 5/608 |
| 3,206,188 A | * | 9/1965 | Douglass, Jr. | 5/614 |
| 3,226,734 A | | 1/1966 | Coventon | 5/607 |
| 3,238,539 A | | 3/1966 | Koch | 5/607 |
| 3,286,707 A | | 11/1966 | Shafer | 601/5 |
| 3,302,218 A | | 2/1967 | Stryker | 5/607 |
| 3,344,445 A | | 10/1967 | Crawford | 5/430 |
| 3,388,700 A | | 6/1968 | Mountz | 601/5 |

(List continued on next page.)

FOREIGN PATENT DOCUMENTS

| | | |
|---|---|---|
| EP | 0 569 308 A1 | 5/1993 |
| FR | 2034679 | 12/1970 |
| FR | 2 247 194 | 5/1975 |
| FR | 2 549 366 | 1/1985 |
| FR | 2 585 240 | 1/1987 |
| TW | 7786 | 11/1975 |
| WO | WO 93/05745 | 9/1992 |

Primary Examiner—Robert G. Santos
(74) Attorney, Agent, or Firm—Bose McKinney & Evans LLP

(57) ABSTRACT

A patient support apparatus comprises a base, and a patient support assembly coupled to the base for pivotable movement about a pivot axis generally transverse to a longitudinal axis of the patient support assembly. A pivot mechanism is coupled to the patient support assembly to rotate the patient support assembly about the pivot axis. A controller is coupled to the pivot mechanism to control rotation of the patient support assembly about the pivot axis at a selected rate of rotation and to a selected angle of rotation to provide rotational therapy to the patient.

41 Claims, 13 Drawing Sheets

U.S. PATENT DOCUMENTS

| | | | |
|---|---|---|---|
| 3,434,165 A | 3/1969 | Keane | 5/608 |
| 3,451,070 A | 6/1969 | Danielson | 5/83.1 |
| 3,499,529 A | 3/1970 | Katzfey et al. | 5/617 |
| 3,584,321 A | 6/1971 | Buchanan | 5/601 |
| 3,653,079 A | 4/1972 | Bourgraf et al. | 5/627 |
| 3,658,052 A | 4/1972 | Alter | 600/534 |
| 3,737,924 A | 6/1973 | Davis | 5/108 |
| 3,739,406 A | 6/1973 | Koetter | 5/608 |
| 3,748,666 A | 7/1973 | Seng | 5/609 |
| 3,752,153 A | 8/1973 | Copeland | 601/5 |
| 3,765,406 A | 10/1973 | Toole et al. | 601/5 |
| 3,783,863 A | 1/1974 | Kliever | 128/847 |
| 3,814,414 A | 6/1974 | Chapa | 5/601 |
| 3,820,176 A | 6/1974 | Feiertag | 5/611 |
| 3,827,089 A | 8/1974 | Grow | 5/607 |
| 3,828,377 A | 8/1974 | Eary, Sr. | 5/632 |
| 3,832,742 A | 9/1974 | Stryker | 5/610 |
| 3,851,644 A | 12/1974 | Slagle | 128/847 |
| 3,868,103 A * | 2/1975 | Pageot et al. | 5/614 |
| 3,874,010 A | 4/1975 | Geary | 5/610 |
| 3,884,225 A | 5/1975 | Witter | 5/630 |
| 3,902,204 A | 9/1975 | Lee | 5/86.1 |
| 3,905,591 A | 9/1975 | Schorr et al. | 5/601 |
| 3,940,808 A | 3/1976 | Petrini | 5/83.1 |
| 3,941,365 A | 3/1976 | Frymoyer | 5/610 |
| 4,071,916 A * | 2/1978 | Nelson | 5/658 |
| 4,080,673 A | 3/1978 | Weisler | 5/658 |
| 4,084,274 A | 4/1978 | Willis et al. | 5/609 |
| 4,109,329 A | 8/1978 | Tupper | 5/607 |
| 4,152,795 A | 5/1979 | Rodosta et al. | 5/658 |
| 4,156,815 A | 5/1979 | Hogan | 5/601 |
| 4,175,550 A | 11/1979 | Leininger et al. | 601/5 |
| 4,183,110 A | 1/1980 | Kidd et al. | 5/629 |
| 4,195,829 A * | 4/1980 | Reser | 5/614 |
| 4,244,358 A | 1/1981 | Pyers | 606/242 |
| 4,274,167 A | 6/1981 | Immel | 5/610 |
| 4,277,857 A | 7/1981 | Svehaug | 5/610 |
| 4,356,577 A | 11/1982 | Taylor et al. | 5/608 |
| 4,384,378 A | 5/1983 | Getz et al. | 5/86.1 |
| 4,395,786 A | 8/1983 | Casey et al. | 5/616 |
| 4,432,353 A | 2/1984 | Vrzalik | 601/5 |
| 4,490,867 A | 1/1985 | Gabrielsson | 5/509.1 |
| 4,535,762 A * | 8/1985 | Natchev | 606/244 |
| 4,557,471 A * | 12/1985 | Pazzini | 5/618 |
| 4,558,857 A * | 12/1985 | Heller | 5/618 |
| 4,572,493 A | 2/1986 | Hubert | 5/608 |
| 4,578,833 A | 4/1986 | Vrzalik | 5/607 |
| 4,584,989 A | 4/1986 | Stith | 600/18 |
| 4,586,492 A | 5/1986 | Manahan | 601/90 |
| 4,619,270 A | 10/1986 | Margolis et al. | 600/534 |
| 4,638,516 A * | 1/1987 | Vrzalik | 5/611 |
| 4,655,206 A | 4/1987 | Moody | 5/628 |
| 4,658,450 A | 4/1987 | Thompson | 5/607 |
| 4,685,159 A * | 8/1987 | Oetiker | 5/608 |
| 4,763,643 A | 8/1988 | Vrzalik | 601/93 |
| 4,769,584 A | 9/1988 | Irigoyen et al. | 318/648 |
| 4,827,541 A | 5/1989 | Vollman et al. | 5/613 |
| 4,841,585 A | 6/1989 | Masuzawa | 5/610 |
| 4,847,929 A * | 7/1989 | Pupovic | 5/608 |
| 4,852,193 A | 8/1989 | Alsip et al. | 5/607 |
| 4,856,128 A | 8/1989 | Alsip et al. | 5/607 |
| 4,866,796 A | 9/1989 | Robinson et al. | 5/607 |
| 4,868,937 A | 9/1989 | Connolly | 5/608 |
| 4,872,657 A | 10/1989 | Lussi | 5/608 |
| 4,912,754 A | 3/1990 | Van Steenburg | 378/209 |
| 4,920,589 A | 5/1990 | LaVelle et al. | 5/607 |
| 4,924,537 A | 5/1990 | Alsip et al. | 5/608 |
| 4,939,801 A | 7/1990 | Schaal et al. | 5/607 |
| 4,941,221 A | 7/1990 | Kanzler | 5/615 |
| 4,944,054 A | 7/1990 | Bossert | 5/609 |
| 4,947,496 A | 8/1990 | Connolly | 5/607 |
| 4,958,817 A | 9/1990 | Heller et al. | 5/607 |
| 4,960,271 A | 10/1990 | Sebring | 5/608 |
| 4,987,622 A | 1/1991 | Shockey | 5/86.1 |
| 5,005,233 A | 4/1991 | Toivio et al. | 5/83.1 |
| 5,018,712 A | 5/1991 | Schaefer | 5/607 |
| 5,020,170 A | 6/1991 | Ruf | 5/607 |
| 5,023,968 A | 6/1991 | Diehl et al. | 5/81.1 R |
| 5,048,071 A | 9/1991 | Van Steenburg | 378/209 |
| 5,060,324 A | 10/1991 | Marinberg et al. | 5/81.1 T |
| 5,088,706 A | 2/1992 | Jackson | 5/608 |
| 5,092,007 A | 3/1992 | Hasty | 5/715 |
| 5,103,511 A | 4/1992 | Sequin | 5/607 |
| 5,131,103 A | 7/1992 | Thomas et al. | 5/601 |
| 5,131,105 A | 7/1992 | Harrawood et al. | 5/607 |
| 5,131,106 A | 7/1992 | Jackson | 5/613 |
| 5,148,815 A | 9/1992 | Britton | 5/628 |
| 5,152,024 A | 10/1992 | Chrones et al. | 5/609 |
| 5,181,288 A | 1/1993 | Heaton et al. | 5/607 |
| 5,208,928 A | 5/1993 | Kuck et al. | 5/608 |
| 5,230,112 A | 7/1993 | Harrawood et al. | 5/607 |
| 5,230,113 A * | 7/1993 | Foster et al. | 5/608 |
| 5,274,862 A | 1/1994 | Palmer, Jr. et al. | 5/81.1 R |
| 5,299,334 A | 4/1994 | Gonzalez | 5/607 |
| 5,319,817 A | 6/1994 | Hay et al. | 5/611 |
| 5,334,186 A | 8/1994 | Alexander | 604/180 |
| 5,398,356 A * | 3/1995 | Pfleger | 5/608 |
| 5,404,603 A | 4/1995 | Fukai et al. | 5/609 |
| 5,412,823 A | 5/1995 | Sitta | 5/601 |
| 5,418,990 A | 5/1995 | Risasen | 5/608 |
| 5,427,338 A | 6/1995 | Garrett et al. | 248/68.1 |
| 5,502,853 A | 4/1996 | Singleton et al. | 5/609 |
| 5,515,561 A | 5/1996 | Saggitt et al. | 5/607 |
| 5,515,869 A | 5/1996 | Powell et al. | 5/628 |
| 5,621,932 A | 4/1997 | Strachan | 5/600 |
| 5,621,933 A * | 4/1997 | Knapp et al. | 5/608 |
| 5,664,270 A | 9/1997 | Bell et al. | 5/600 |
| 5,699,568 A | 12/1997 | Couldridge | 5/628 |
| 6,065,165 A | 5/2000 | Delk et al. | 5/628 |
| 6,108,838 A | 8/2000 | Connolly et al. | 5/609 |
| 6,112,349 A | 9/2000 | Connolly | 5/607 |
| 6,260,220 B1 * | 7/2001 | Lamb et al. | 5/607 |
| 6,282,736 B1 * | 9/2001 | Hand et al. | 5/608 |
| 6,353,949 B1 * | 3/2002 | Falbo | 5/610 |
| 6,385,801 B1 * | 5/2002 | Watanabe et al. | 5/607 |
| 2002/0026671 A1 * | 3/2002 | Hand et al. | 5/608 |

* cited by examiner

HOSPITAL BED

This application is a continuation of U.S. application Ser. No. 09/499,200, filed Feb. 7, 2000, now U.S. Pat. No. 6,282,736, which is a continuation PCT Application Ser. No. PCT/US98/16497, filed Aug. 7, 1998, which claims the benefit of U.S. provisional application Ser. No. 60/055,043 filed Aug. 8, 1997 and U.S. provisional application Ser. No. 60/090,212 filed Jun. 22, 1998.

BACKGROUND AND SUMMARY OF THE INVENTION

The present invention relates to a hospital bed. More particularly, the present invention relates to a bed which permits rotation of a patient supported on a patient support surface of the bed.

According to an illustrated embodiment of the invention, a support apparatus includes a base, and a support assembly coupled to the base. The support assembly includes a patient support surface configured to support a patient. The bed further includes means for simultaneously rotating the patient support assembly about a first axis generally parallel to a longitudinal axis of the patient support assembly, and rotating the patient support assembly about a second axis generally transverse to the longitudinal axis of the patient support assembly alternately in a first direction and a second direction to provide rotational therapy to the patient about both the first and second axes.

According to yet another illustrated embodiment of the invention, a support apparatus includes a base, a support assembly coupled to the base for pivotable movement about a pivot axis generally transverse to a longitudinal axis of the patient support assembly, a pivot mechanism, and a controller. The support assembly includes a patient support surface configured to support a patient. The pivot mechanism is coupled to the support assembly to rotate the support assembly about the pivot axis. The controller is coupled to the pivot mechanism and is programmable to cause rotation of the support assembly about the pivot axis alternatively in a first direction and a second direction to provide rotational therapy to the patient.

According to another illustrated embodiment of the invention, a proning apparatus includes a proning device having a first surface configured to be located adjacent a posterior side of the patient to support the patient in a supine position and a proning surface configured to be located adjacent an anterior side of the patient to support the patient in a prone position. The apparatus further includes at least one air bladder located on the first surface, at least one air bladder located on the proning surface, and a controller configured to alternatively inflate and deflate the at least one air bladder located on the first surface and the at least one air bladder located on the proning surface according to a sequence defined by a compression therapy for the patient.

According to yet another illustrated embodiment of the invention, a patient support apparatus includes a base, a patient support assembly coupled to the base, a first drive mechanism, and a second drive mechanism. The patient support assembly includes a patient support surface configured to support a patient. The first drive mechanism is configured to rotate the patient support assembly about a first axis generally parallel to a longitudinal axis of the patient support assembly. The second drive mechanism is configured to rotate the patient support assembly about a second axis generally transverse to the longitudinal axis of the patient support assembly while the first drive mechanism rotates the patient support assembly about the first axis to provide rotational therapy to the patient about both the first and second axes.

According to another illustrated embodiment of the invention, a patient support apparatus includes a base, a patient support assembly coupled to the base, and an electrical controller. The patient support assembly has a patient support surface configured to support a patient. The controller is coupled the patient support assembly to cause simultaneous rotation of the patient support assembly about a first axis generally parallel to a longitudinal axis of the patient support assembly and about a second axis generally transverse to the longitudinal axis of the patient support assembly to provide rotational therapy to the patient about both the first and second axes.

Finally, according to another illustrated embodiment of the invention, a method for providing rotational therapy to a patient includes the steps of providing a patient support apparatus having a base and a patient support surface coupled to the base, positioning the patient on the patient support surface, alternately rotating the patient support assembly in a first direction and a second direction about a transverse axis generally parallel to a transverse axis of the patient support assembly.

Additional objects, features, and advantages of the invention will become apparent to those skilled in the art upon consideration of the following detailed description of the illustrated embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
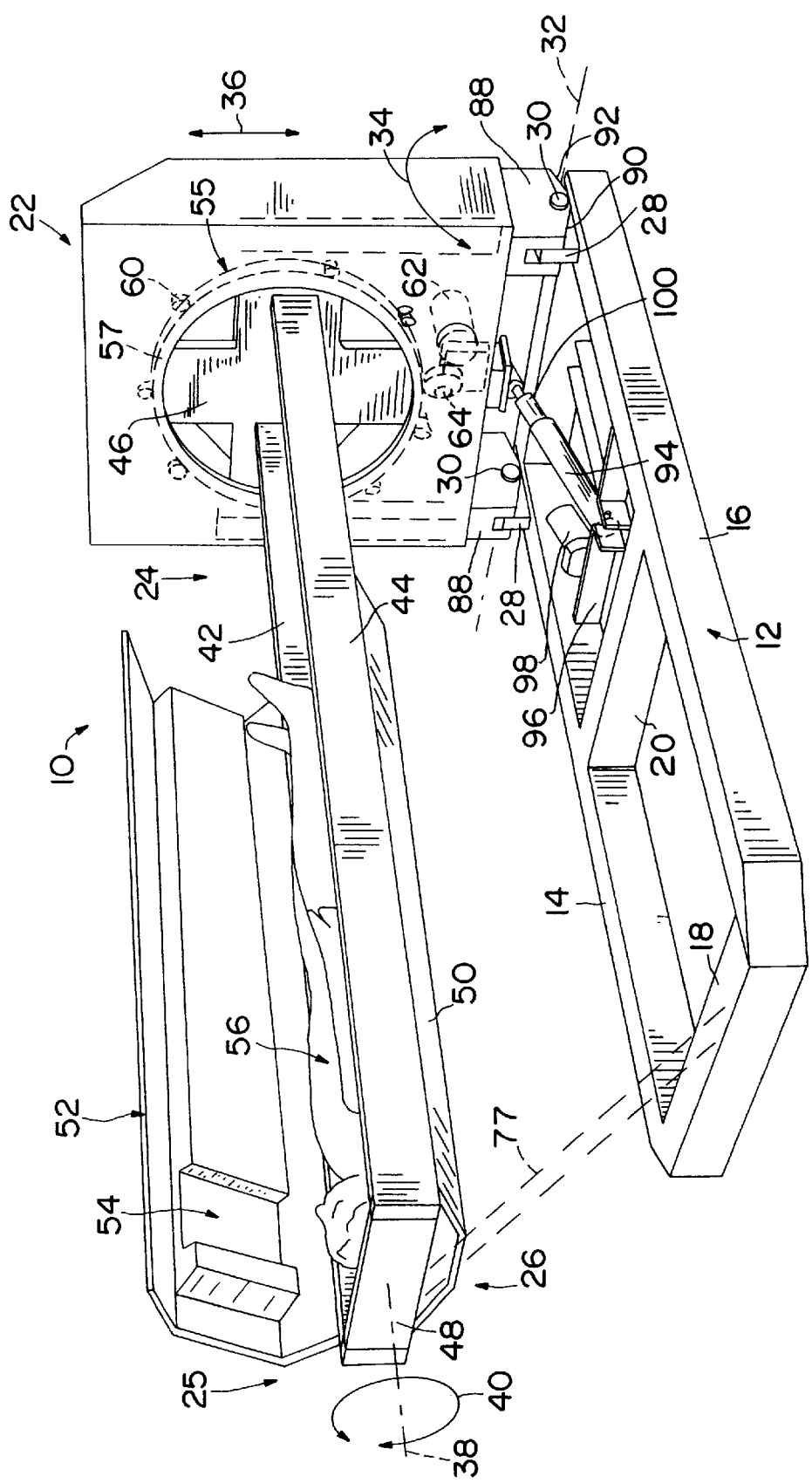
FIG. 1 is a perspective view illustrating a proning bed of the present invention.

Referring now to the drawings, FIG. 1 illustrates a bed 10 having a base 12 which includes opposite side members 14 and 16 and cross members 18 and 20 extending between side members 14 and 16. A support assembly 22 is located at a foot end 24 of bed 10. Support assembly 22 supports a patient support assembly 26 in a cantilevered fashion. Therefore, the head end 25 of bed 10 is open to facilitate access to the patient 56.

Support assembly 22 is pivotably coupled to pivot blocks 28 of base 12 by pivot connections 30. Therefore, support assembly 22 can pivot about axis 32 in the directions of double-headed arrow 34. As discussed in detail below, the support assembly 22 is movable up and down in the direction of double-headed arrow 36 to raise and lower the height of patient support assembly 26 Also as discussed below in detail, support assembly 22 can rotate the patient support assembly 26 about its longitudinal axis 38 as indicated by double-headed arrow 40. Support assembly 22 can rotate the patient support assembly 26 in either direction a full 360°.

Patient support assembly 26 includes a pair of horizontally extending arms 42 and 44 which are coupled to a cruciform-shaped plate 46 of support assembly 22. Arms 42 and 44 extend away from support assembly 22 in a cantilevered fashion. An end beam 46 extends between arms 42 and 44 at a distal end of patient support assembly 26 A patient support surface 50 is coupled between arms. When it is desired to rotate a patient, a proning support surface 52 is also coupled between arms 42 and 44. Proning support surface 52 includes a recess 54 for receiving the head of a patient 56. Support surfaces 50 and 52 are shown in an illustrative representation only. It is understood that support surfaces 50 and 52 will include selective placement of foam, air bladders, fluidized bladders, or other suitable support surfaces to reduce pressure on the patient 56 and/or support an unstable spine of the patient 56. The support surfaces 50 and 52 may include contoured support surfaces to minimize pressure on the patient. Layers of air and beads can be positioned over the contoured support surfaces. A vacuum can be selectively applied to the bead packs to further conform the support surfaces to the patient.

Figure 2:
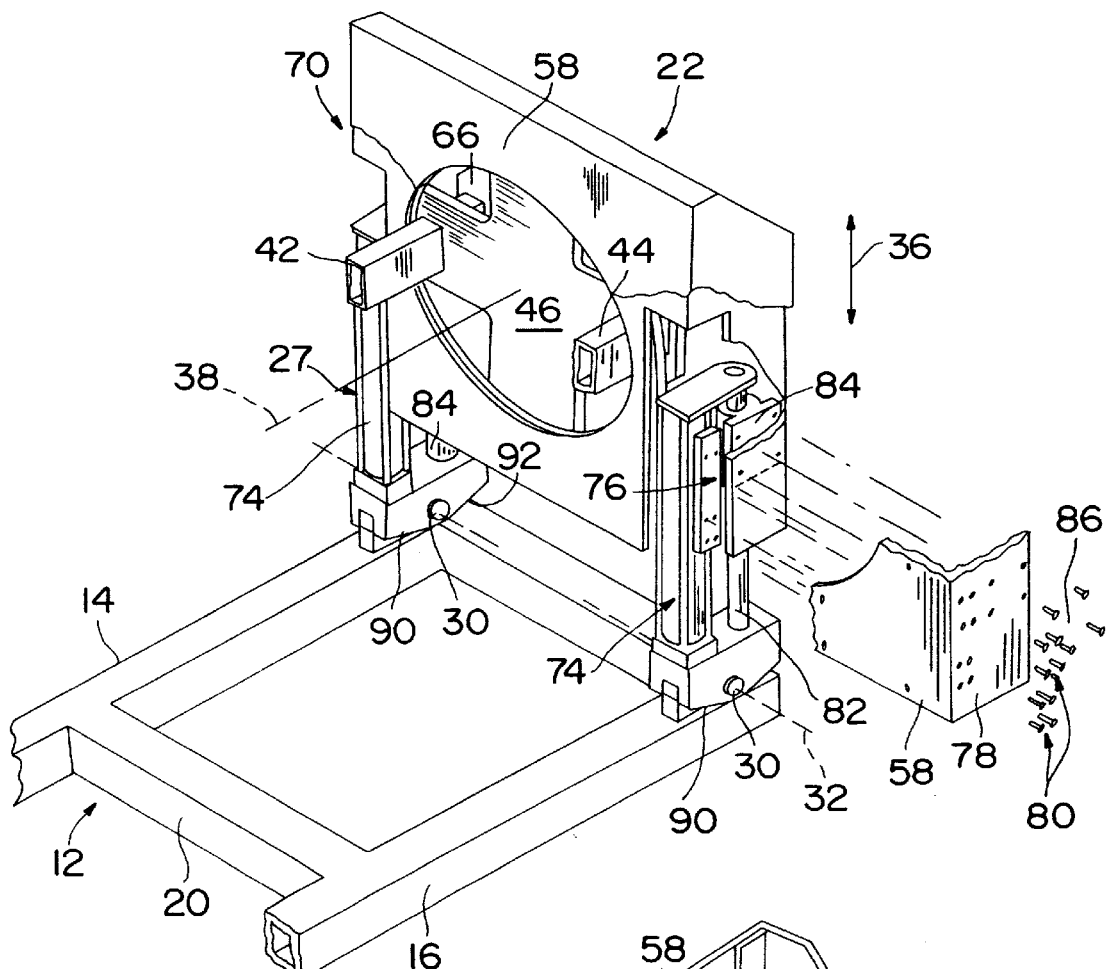
FIG. 2 is a perspective view, with portions broken away, illustrating a base and a patient support surface support assembly located at a foot end of the bed to control movement of the patient support surface.
Figure 3:
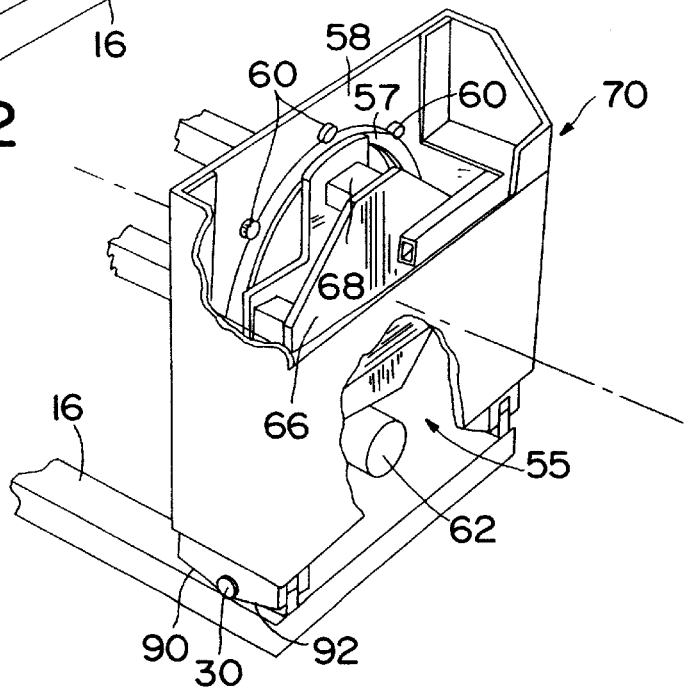
FIG. 3 is a perspective view, with portions broken away, illustrating additional details of the support assembly of the present invention.

Cruciform 46 is coupled to a drive mechanism 55 including rotatable, annular rack 57 which is held in place on a front surface 58 of support assembly 22 by rotatable bearings 60 which are coupled to front surface 58. Cruciform 46 includes four arms which are each secured to the annular rack 57. A motor 62 and gear 64 are located on support assembly 22. Gear 64 engages annular rack 57 to rotate the annular rack 57 relative to the front surface 58. Therefore, the support arms 42 and 44 coupled to the cruciform also rotate in the direction of doubleheaded arrow 40. As illustrated in FIGS. 2 and 3, the arms 42 and 44 extend through the cruciform 46 and are then welded to the cruciform 46. Arms 42 and 44 are also welded to a rear support plate 66. Extension sections 68 are welded between the support plate 66 and the cruciform 46 at locations between the support arms 42 and 44.

The support assembly 22 includes a movable frame 70 which is movable relative to outer supports 72. FIG. 2 illustrates the frame 70 in an upwardly extended position.

Opposite outer supports 72 each include a rodless cylinder 74 having a movable carriage 76. Movable carriage 76 is coupled to a sidewall 78 of movable frame 70 by fasteners 80. A guide cylinder 82 is located adjacent each rodless cylinder 74. A guide block 84 slides over each cylinder 82. Guide block 84 is coupled to sidewall 78 of frame 70 by fasteners 86.

illustratively, rodless cylinders 74 are Lintra® rodless cylinder available from Norgren located in Rockford, Ill. An air supply is used to control movement of the carriages 76 on the rodless cylinders 74 to move the movable frame 70 of the support assembly 22 up and down in the directions of double-headed arrow 36. Since the annular rack 57, the cruciform 46 and the patient support assembly 26 are all coupled to the movable frame 70, the support surface 26 moves up and down in the direction of double-headed arrow 36 with the movable frame 70. Illustratively, the cylinders 74 provide and 8–9 inch lift. It is understood that hydraulics, lead screws, or other suitable lifting mechanisms can be used with the present invention.

The cantilevered design of the present invention advantageously suspends the patient support surface 26 from the support assembly 22. This permits full body C-arm access. In addition, a head end 25 of the bed is accessible for performing procedures on the patient 56. A support bar 77 can extend between the head end 25 of patient-support surface 26 and base 12 if desired. The support bar 77 can be moved into the support position engaging support surface assembly 26 while the patient 56 is on support surface 50. The support bar 77 can be removed from support surface assembly 26 for C-arm access or rotation.

Figure 4:
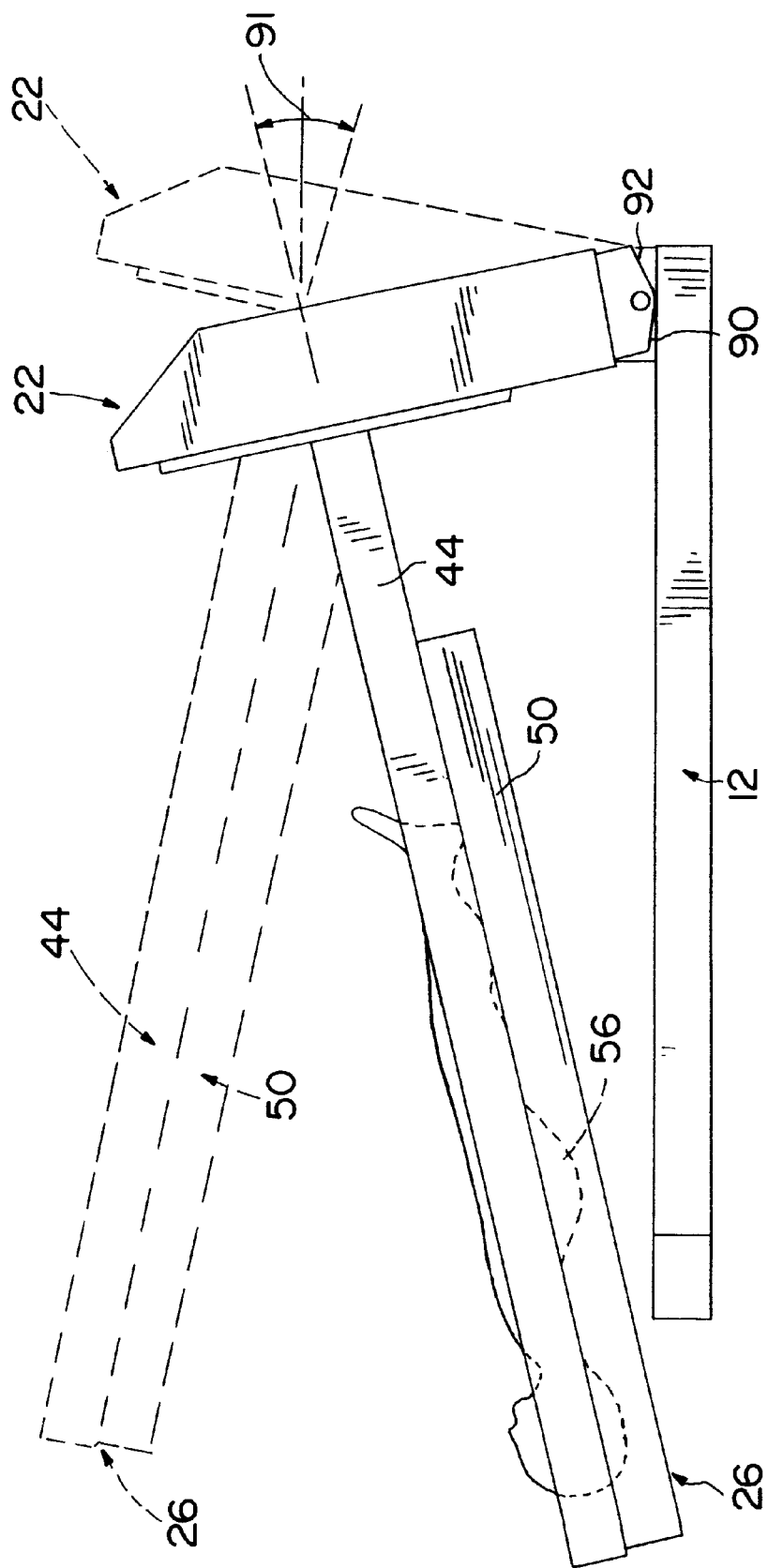
FIG. 4 is a side elevational view illustrating movement of the support assembly to position the patient support surface in either a Trendelenburg or a reverse Trendelenburg position.

The support assembly 22 is coupled to base 12 by blocks 88. Blocks 88 include a front angled stop 90 and a rear angled stop 92 which limit pivotable movement of the support assembly 22 relative to the base 12. As illustrated in FIG. 4, the support assembly 22 is pivotable relative to base 12 to move the patient support assembly 26 between a Trendelenburg position illustrated in solid lines in FIG. 4 to a reverse Trendelenburg position illustrated in dotted lines in FIG. 4. Illustratively, the pivotable movement is about +/−15° relative to horizontal in either direction as illustrated by angles 91 in FIG. 4. Front stop 90 engages base 12 when the patient support surface is in the Trendelenburg position shown in solid lines in FIG. 4. Second stop 92 engages the base 12 when the support assembly is in the reverse Trendelenburg position as shown in dotted lines in FIG. 4.

Pivotable movement of support assembly 22 about axis 32 is controlled by a cylinder 94 pivotably coupled to a cross member 96 which extends between arms 14 and 16 of base 12, A fluid source 98 is also coupled to cross member 96 to control movement of a piston 100 relative to cylinder 94 between an extended position and a retracted position. Piston 100 is pivotably coupled to support assembly 22. Therefore, retraction of piston 100 causes movement of the support assembly 22 forward to the Trendelenburg position. Extension of piston 100 causes pivotable movement of the support assembly 22 to the reverse Trendelenburg position.

Figure 5:
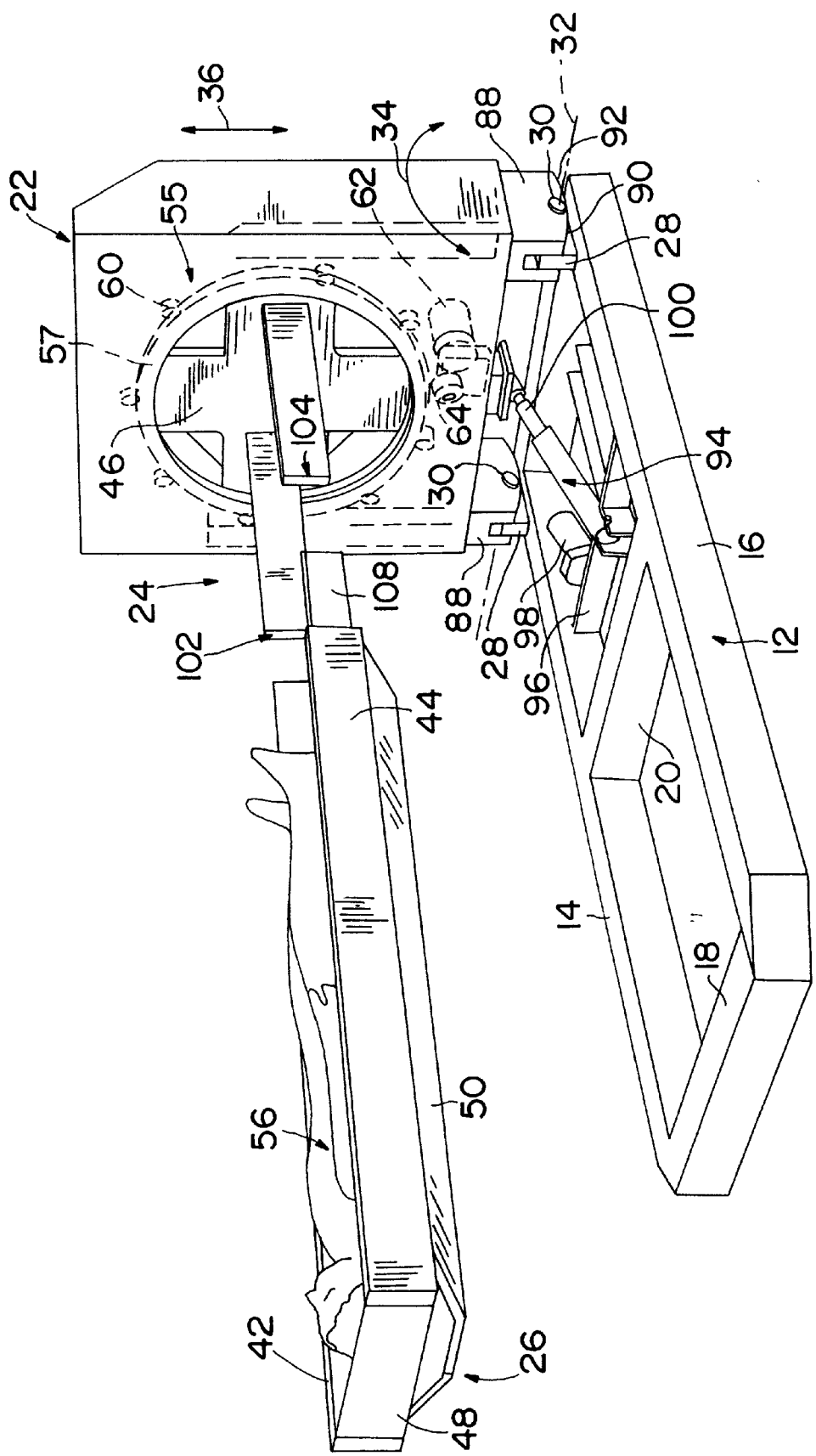
FIG. 5 is a perspective view illustrating another embodiment of the present invention in which a modular patient support assembly is configured to be coupled to receptacles on the support assembly.

Although the side arms 42 and 44 of the patient support assembly 26 are shown as solid arms in FIG. 1, it is understood that the side arms 42 and 44 may be shorter pieces cut off adjacent support assembly 22 as illustrated by arms 102 and 104 in FIG. 5. Since arms 102 and 104 are illustratively hollow receptacles, the remainder of the patient support assembly 26 includes arm extensions 106 and 108 which slide into the open ends of receptacle arms 102 and 104 extending from support assembly 22. Therefore, a patient could be transported directly from a trauma situation on the patient support surface 50 using suitable handles (not shown). The patient support assembly 26 and surface 50 may then be attached to the open ends of arms 102 and 104 and secured in position to form a cantilevered support surface 26 for the patient 56 without having to move the patient 56 from the support surface 50. Operation of the bed is then as described above.

The bed can be programmed to provide rotational therapy to the patient. The bed can also be used to prone the patient 56 so that the patient lies face down on the proning support surface 52.

In FIGS. 6–15, these elements referenced by numbers from FIGS. 1–5 perform the same or similar function. Patient support assembly includes a lower set of doors 110 and an upper set of doors 112. Lower set of doors 110 supports the patient support surface 50 for holding the patient in a supine position. Doors 110 and 112 are pivotably coupled to lifting apparatus 114 and 116. A first lifting apparatus 114 is coupled to arm 42, and a second lifting apparatus 116 is coupled to arm 44. Each lifting apparatus 114 and 116 includes an outer rectangular support 118 having a top surface 120 and a bottom surface 122. Each lifting apparatus 114, 116 further includes first and second lifting cylinder assemblies 124 and 126 located within side arms 42, 44, respectively. The first and second cylinder assemblies 124 and 126 each include a pair of cylinders 128, 130 which are coupled to arms 42, 44 by pivot connections 132 and 134, respectively. Cylinders 128 and 130 include pistons 136 and 138, respectively, which are pivotably coupled to top surface 120 of movable support 118 at locations 140. Illustratively, cylinders 128, 130 are hydraulic cylinders controlled by a suitable controller located within support assembly 22. Lines for controlling cylinders 128, 130 can be run through the arms 142, 144 to minimize line clutter.

Figure 6:
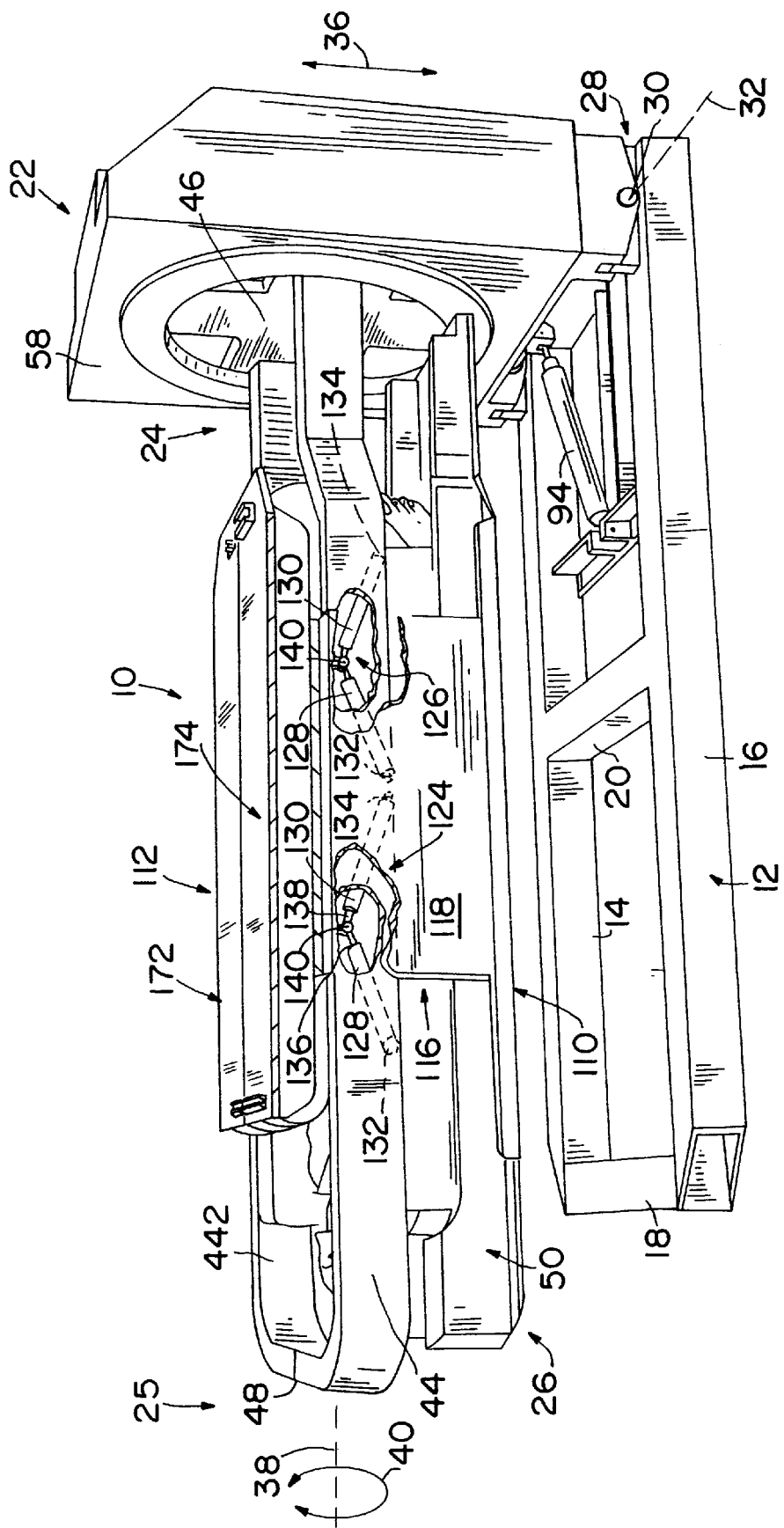
FIG. 6 is a perspective view illustrating a proning bed of the present invention, with a patient on a support surface in a supine position.
Figure 10:
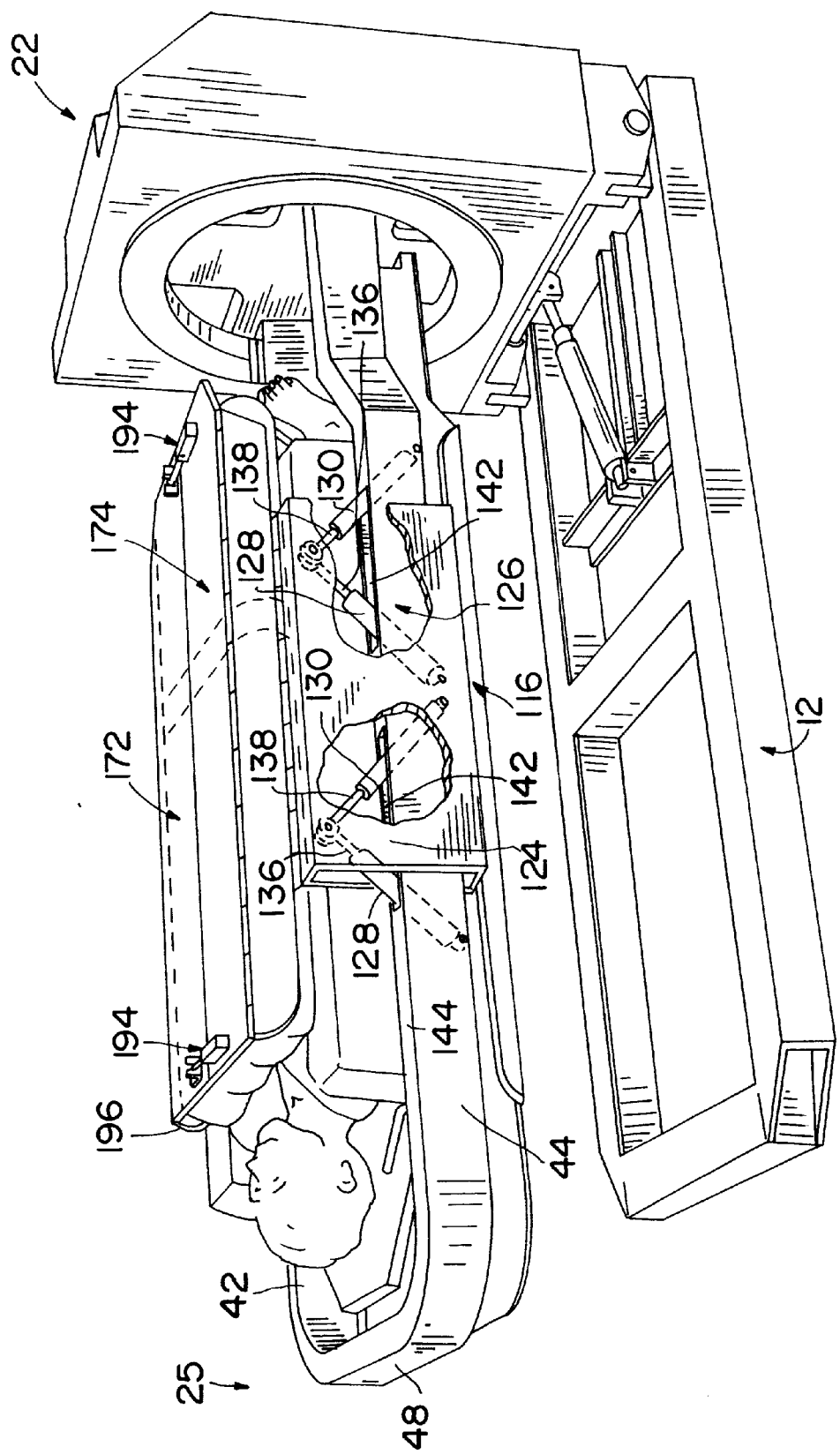
FIG. 10 is a perspective view similar to FIG. 6, illustrating the patient support surface in its raised position relative to the side arms of the bed.

The pistons 136, 138 are movable from a retracted position illustrated in FIG. 6 to an extended position illustrated in FIG. 10. In the retracted positions, pistons 136 and 138 position the support surface 50 at a lowermost position relative to arms 42 and 44 of the frame. In the extended position, the pistons 136 and 138 lift the movable support 118 and the patient support surface 60 coupled thereto upwardly to the position shown in FIG. 10. Arms 42 and 44 each are configured to include apertures 142 shown in FIG. 5 to permit the cylinders 128, 130 and pistons 136, 138 to move upwardly past a top surface 144 of frame arms 42, 44.

Figure 7:
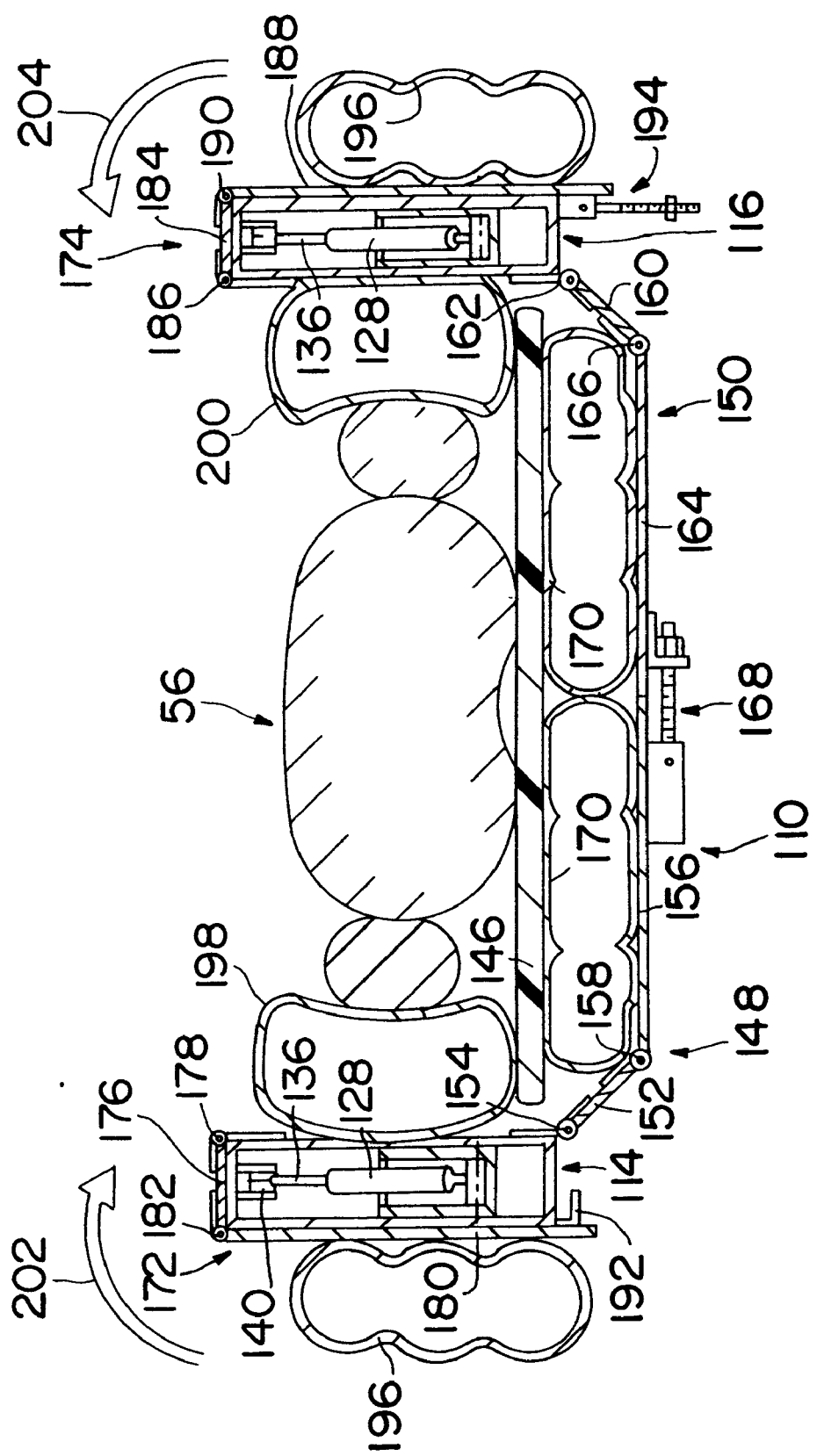
FIG. 7 is a sectional view taken through the patient support assembly of FIG. 1 illustrating top doors in an open position.

The bed 10 is configured so that a patient can be transported from a remote trauma location and positioned directly on the bed as illustrated in FIG. 7. Illustratively, the patient is transported to the bed 10 on a backboard 146. Illustratively, the backboard 146 may include air bladders, foam padding, and/or contoured sections to facilitate transport of the patient and to provide a pressure reducing surface when the backboard 146 is located on the bed 10. The backboard 146 may Illustratively include a self-inflating surface, such as a Therm-A-Rest® mattress, for use in the field. When the backboard 146 is loaded into the bed 10, connectors are provided for coupling air bladders on the backboard to the air supply system and valves already located on the bed 10. Connectors are also provided for coupling the backboard 146 to the bed 10 mechanically and electrically.

As illustrated in FIG. 7, the bottom door assembly 110 includes a first door 148 pivotably coupled to the first lifting mechanism 114 and a second door 150 pivotably coupled to the second lifting mechanism 116. The first door 148 includes a first section 152 pivotably coupled to the first lifting mechanism 114 by hinge 154 and a second portion 156 pivotably coupled to the first portion 152 by hinge 158. Second door 150 includes a first portion 160 pivotably coupled to the second lifting mechanism 116 by hinge 162 and a second portion 164 pivotably coupled to the first portion 160 by hinge 166. Latches 168 are used to secure the first and second doors 148 and 150 in a closed position illustrated in FIG. 7 to provide a support for the backboard 146. Illustratively, a pair of air bladders 170 are located on an inner surface of doors 148 and 150 to provide a support for backboard 146. Alternatively, the patient can be situated directly on the air bladders 170 if the patient has not been transported to the bed on the backboard 146.

The proning doors 112 similarly include a first door 172 and a second door 174 shown in an open position in FIG. 7. Door 172 includes a first portion 176 pivotably coupled to first lifting apparatus 114 by hinge 178. Door 172 further includes a second portion 180 pivotably coupled to first portion 176 by hinge 182. Door 174 includes a first portion 184 coupled to second lifting apparatus 116 by hinge 186 and a second portion 188 pivotably coupled to first portion 184 by hinge 190. A first latch portion 192 is coupled to second door portion 180 of door 172, and a second latch portion 194 is coupled to second door portion 188 of second door 174. Air bladders 196 are also coupled to second door portions 180 and 188. FIG. 7 also illustrates a pair of inner inflatable side bladders 198 and 200 located along opposite sides of the patient 56.

FIG. 7 illustrates the top doors 172 and 174 in an open position. In the open position, first door portions 176 and 184 rest upon top surface 120 of the first and second lifting apparatus 114, 116, respectively. Therefore, the second door portions 180 and 188 can lie adjacent outer surfaces 118 of the first and second lifting apparatus 114 and 116, respectively, to conserve space. Air bladders 196 may be deflated to conserve additional space.

Figure 8:
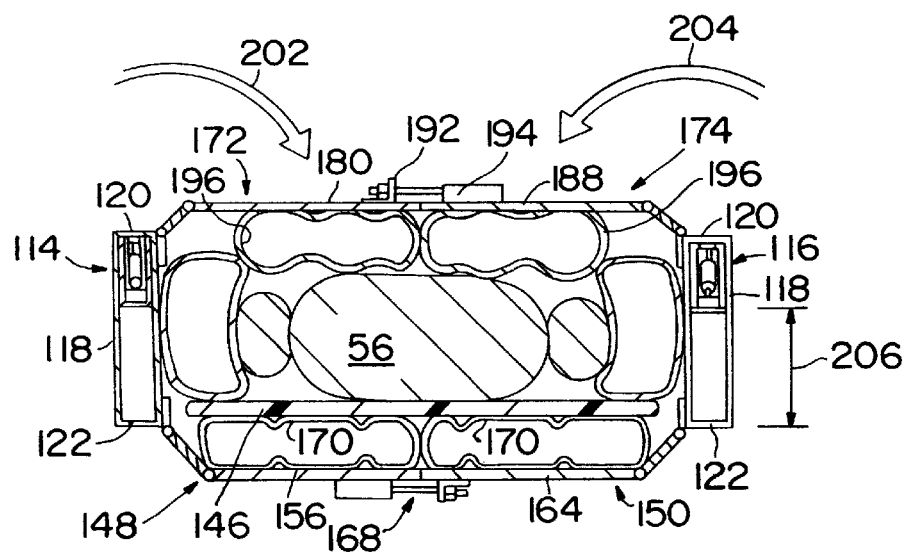
FIG. 8 is a sectional view through the patient support assembly of FIG. 6 with the proning doors in a closed and latched position and with a lifting apparatus on each side of the patient support surface, each lifting apparatus being adjusted to move the patient support surface to its lowermost position relative to support arms of the bed.

After the patient is transported to the bed 10 from an injury site or other location on backboard 146, the patient 56 and the backboard 146 are loaded into the bed 10 as illustrated in FIG. 7 with the patient in the supine position. If it is desired to prone the patient 56 for a medical procedure or therapy, the doors 172 and 174 are closed in the direction of arrows 202 and 204 of FIG. 7, respectively. Once the doors are moved to a closed position illustrated in FIG. 6 and 8–10, latches 192 and 194 are connected to secure the doors 172 and 174 together. It is understood that any type of latch mechanism can be used to hold the doors 172 and 174 in the closed position. As shown in FIG. 8, the air bladders 196 are configured to lie over the patient 56 when the doors 172 and 174 are closed.

In FIG. 8, the pistons 136 and 138 of cylinders 128 and 130, respectively, are in the retracted position shown in FIG. 6. Therefore, the arms 42 and 44 are located adjacent top surface 120 of support 118 of the first and second lifting apparatus 114 and 116. Therefore, bottom surfaces of arms 42 and 44 are spaced apart from a bottom surface 122 of first and second lifting apparatus 114 by a distance 206. In the position of FIGS. 6 and 8, the patient 56 is located at the lowermost support position relative to arms 42 and 44.

Figure 9:
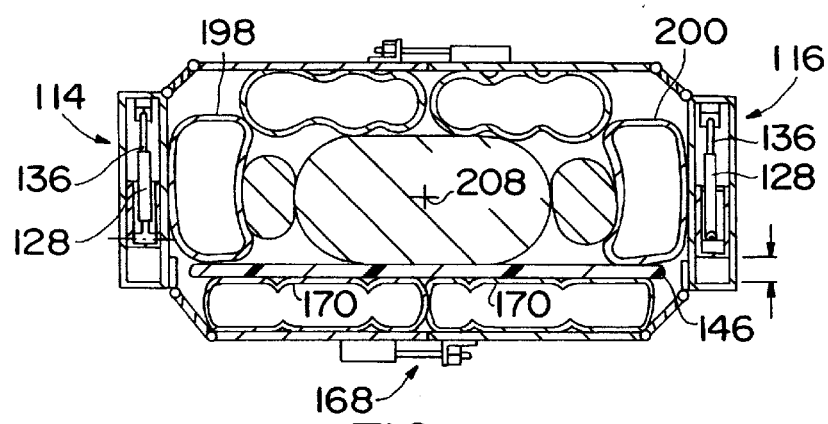
FIG. 9 is a sectional view similar to FIG. 8 in which the lifting apparatus are actuated to move a patient support surface upwardly relative to side support arms of the bed.
Figure 11:
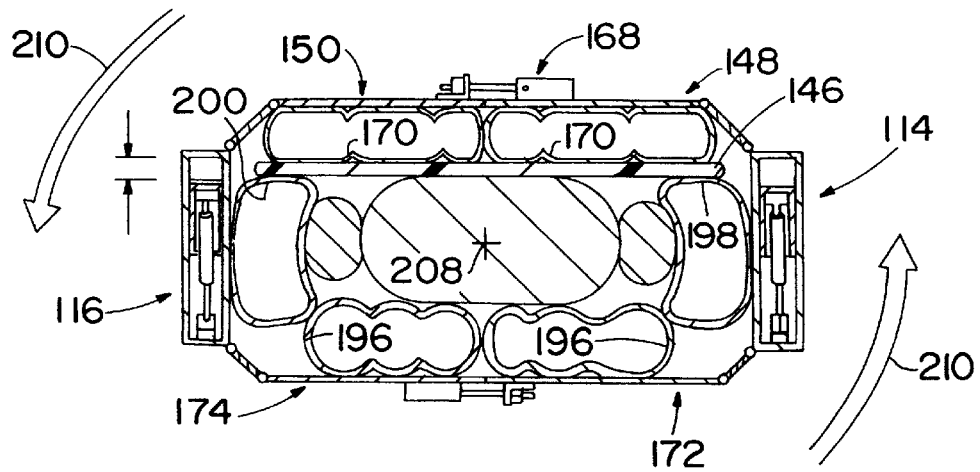
FIG. 11 is a sectional view taken through the patient support surface of FIG. 5, after the bed is operated to rotate the support surface, thereby turning the patient over to a prone position.

When it is desired to rotate or prone the patient, it is desirable to move the patient's center of gravity to a location above a pivot axis 138 of patient support assembly 26. Therefore, before rotating the patient 56, the first and second lifting apparatus 114 and 116 are actuated to extend the pistons 136 and 138 from cylinders 128 and 130 of the first and second cylinder arrangements 124 and 126. By extending the pistons 136 and 138, the top surfaces 120 of supports 118 of the lifting apparatus 114 and 116 move upwardly to the position illustrated in FIGS. 9 and 10. FIG. 9 shows that the distances between the bottom surfaces arms 42 and 44 is closer to the bottom surfaces 122 of supports 118 lifting apparatus 114 and 116 in the FIG. 9 configuration. The patients center of gravity 208 is at or slightly above the location of pivot axis 38. This positioning of patient 56 facilitates the rotating operation and provides less of a falling sensation for the patient 56 as rotation begins.

A controller of the present invention is configured to position the patient properly for proning automatically. A caregiver enters the patient's height and weight using an input device, and then the controller calculates a location of the center of gravity of the patient using known algorithms. The controller then sends appropriate control signals to the cylinders 128 and 130 to lift the patient a desired distance. Once the patient is positioned as illustrated in FIGS. 9 and 10, the controller actuates the drive motor and gear which drives the annular ring and rotates the cruciform 46 and arms 42 and 44 in the direction of arrows 210 in FIG. 11 until the patient has been proned. Once in the prone position of FIG. 11, latches 168 are opened to permit doors 148 and 150 to be moved away from the patient 56. Backboard 146 can then be removed to expose a back of the patient 56. Before the patient is moved to the prone position shown in FIG. 11, an appropriate head support member (not shown) is coupled to the proning doors 112 to support the patient's head and while in the prone position. Alternatively, the length of doors 172 and 174 may be extended and formed to include a recess for receiving the patient's face.

Figure 12:
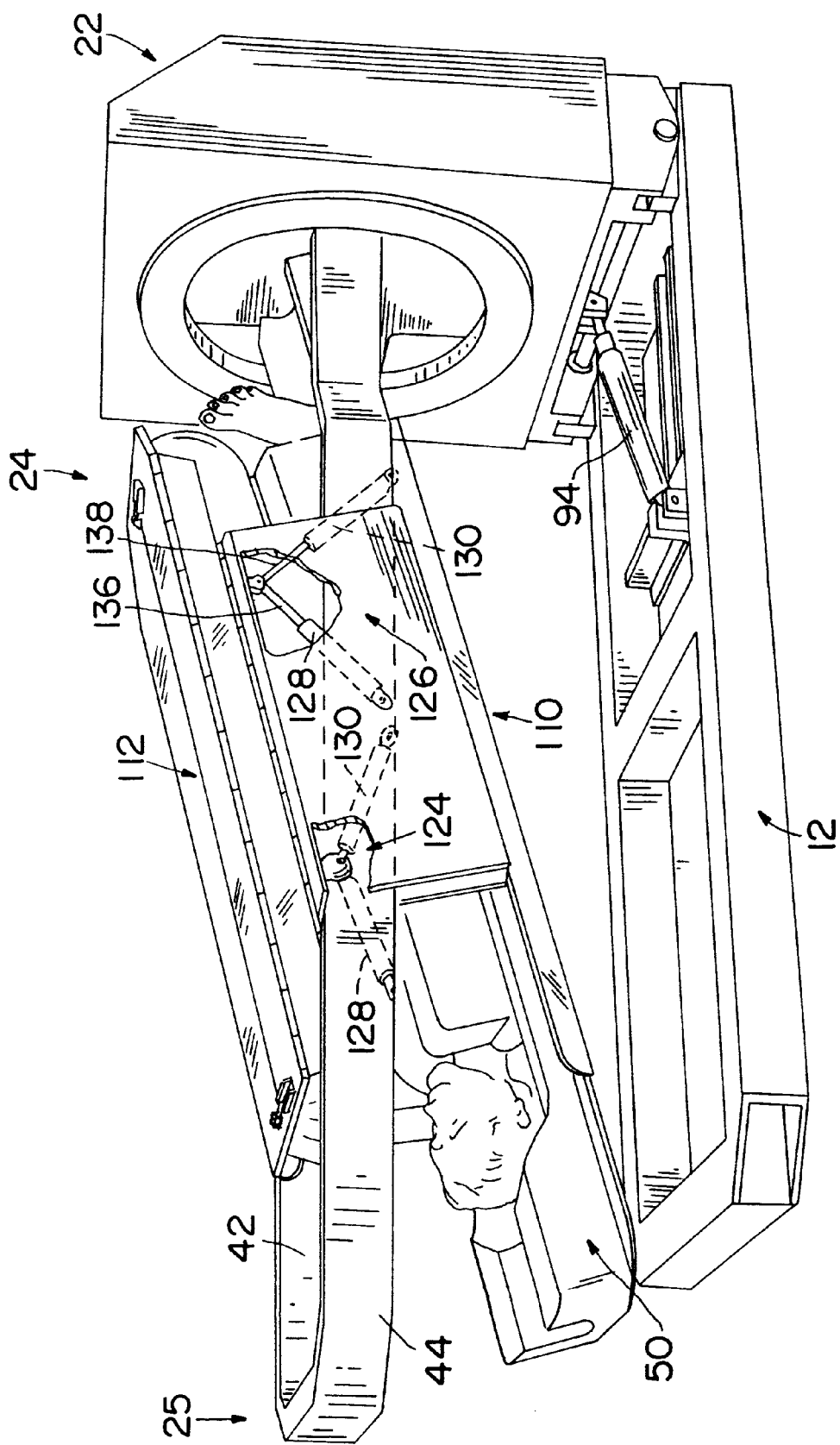
FIG. 12 is a perspective view illustrating the patient support surface of the bed moved to a Trendelenburg position.
Figure 13:
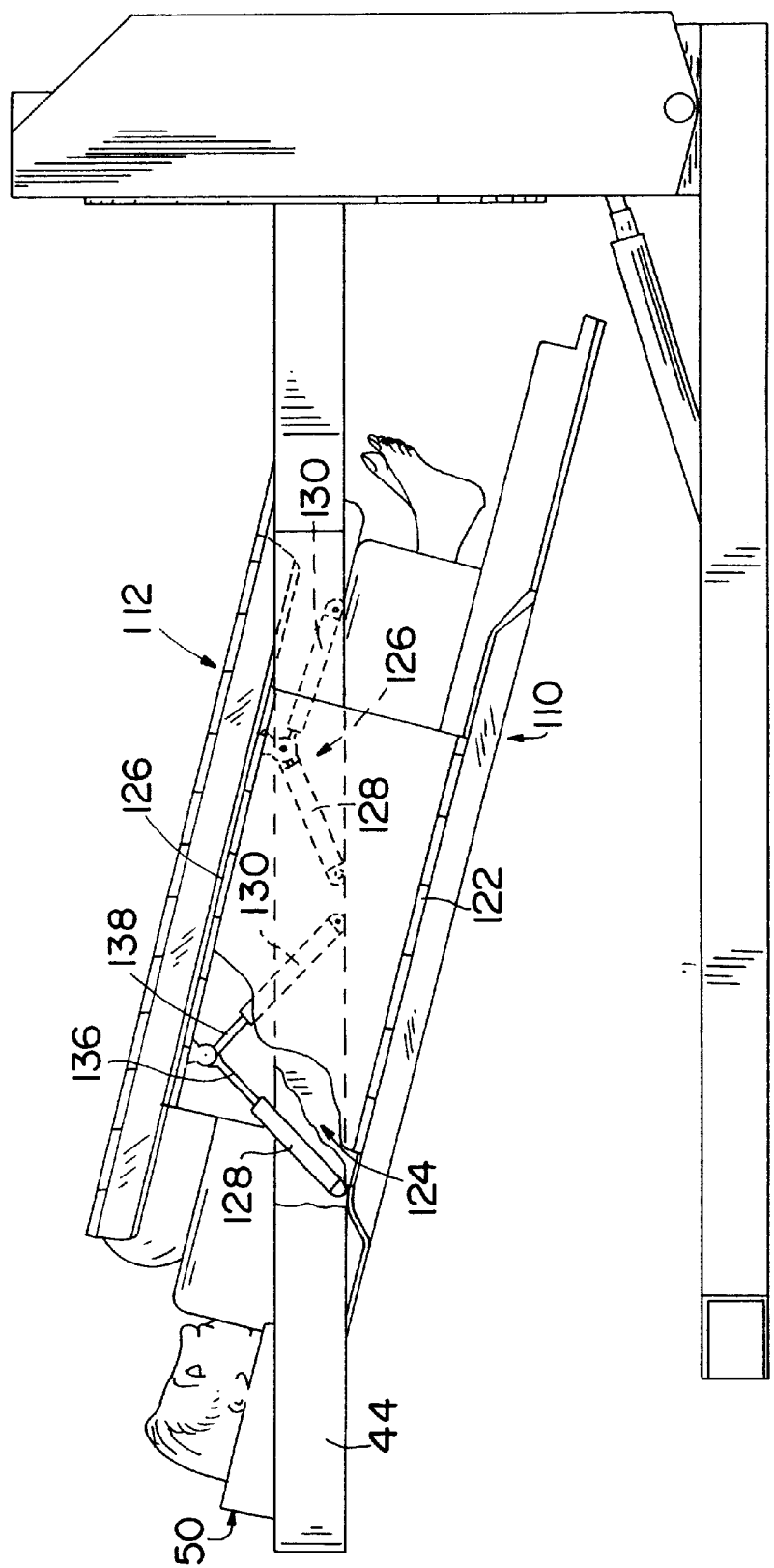
FIG. 13 is a perspective view of the bed of the present invention with the patient support surface in a reverse Trendelenburg position.

As shown in FIGS. 12 and 13, lifting apparatus 114, 116 may also be used for moving the patient support surface 50 from a Trendelenburg position shown in FIG. 12 to a reverse Trendelenburg position shown in FIG. 13. Using the first and second lifting apparatus 114, 116 in this manner eliminates the need for a separate cylinder 94 and a pivotable connection between support 22 and base 12. In other words, the support 22 may be rigidly coupled to base 12 when the first and second lifting apparatus 114 and 116 are used for the Trendelenburg and reverse Trendelenburg positioning.

As shown in FIG. 12, when the pistons 136 and 138 of the first pair of cylinders 124 are in the fully retracted position and the pistons 136 and 138 of the second set of cylinders 126 are in the fully extended position, the patient support surface 50 moves to a Trendelenburg position. Conversely, when the pistons 136 and 138 of the first set of cylinders 124 are moved to fully extended and the pistons 136, 138 and the second set of cylinders 126 are moved to the fully retracted position, the patient support 50 moves to a reverse Trendelenburg position as shown in FIG. 13.

Therefore, the lifting apparatus 114, 116, could also be used to provide rotation of patient 56 about a lateral axis perpendicular to longitudinal axis 38 and the patient 56. In other words, the lifting apparatus 114, 116 can be used to move the patient back and forth between the FIG. 12 position and the FIG. 13 position.

Figure 14:
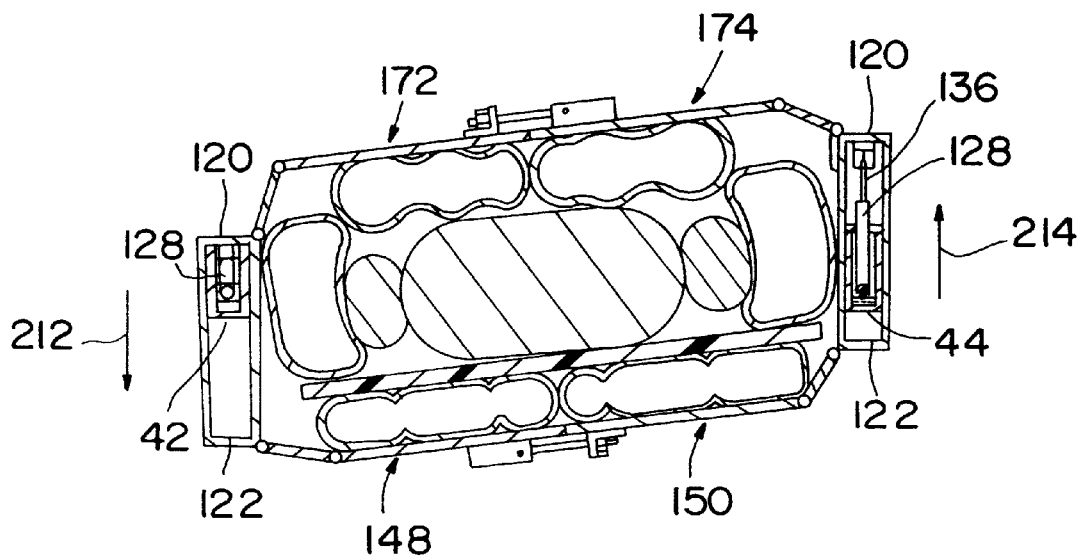
FIGS. 14 and 15 illustrate actuation of a lifting mechanisms on opposite sides of the bed for providing patient rotation using only the lifting mechanisms actuated in opposite, alternating directions.
Figure 15:
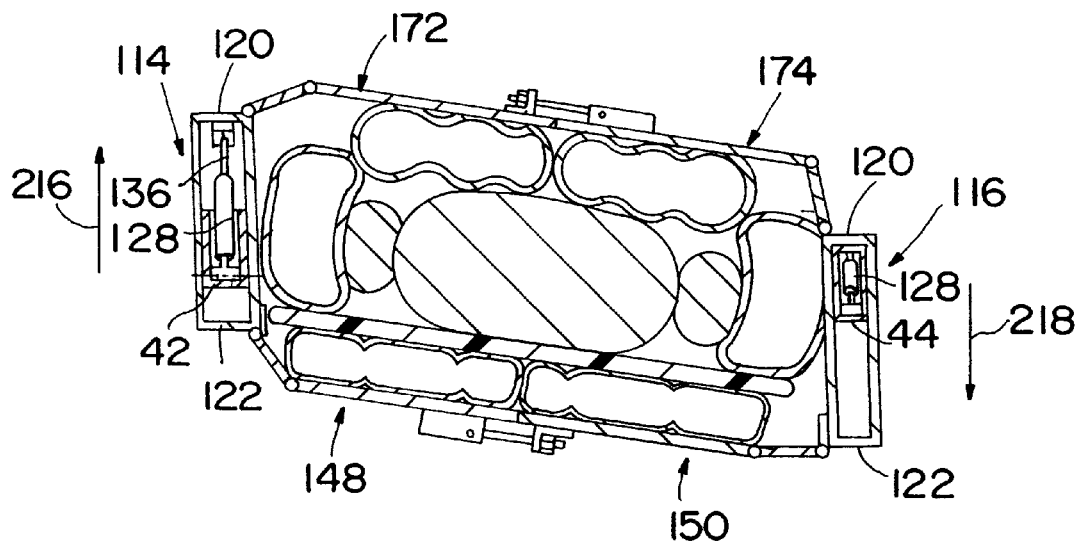

As shown in FIGS. 14 and 15, the first and second lifting apparatus 114, 116 may also be used to provide limited rotational therapy for the patient 56 about axis 38. The main drive motor within support assembly 22 can also be used for rotational therapy. In other words, the entire frame assembly 42, 44, and 46 may be rotated back and forth about axis 38 to provide rotational therapy for the patient. To provide the rotational therapy using only the first and second lifting apparatus 114, 116, the following sequence is used. The pistons 136 and 138 of the first and second cylinder pairs 124 and 126 in lifting apparatus 114 are moved to the retracted position while the pistons 136 and 138 of the cylinders 124 and 126 of lifting apparatus 116 are moved to the extended position as shown in FIG. 14. This causes the support 118 of first lifting apparatus 114 to move downwardly in the direction of arrow 212 and the support 118 of second lifting apparatus 116 to move upwardly in the direction of arrow 214. Next, the pistons 136 and 138 of the cylinder pairs 124 and 126 of lifting apparatus 114 are extended to move the support 118 of lifting apparatus 114 upwardly in the direction of arrow 216 of FIG. 15. Simultaneously, the pistons 136 and 138 of the cylinder pairs 124 and 126 of lifting apparatus 116 are retracted to move the support 1 18 of second lifting apparatus 116 downwardly in the direction of arrow 218. Therefore, as shown in FIGS. 14 and 15, rotational therapy can be provided to the patient 56 by alternately extending and retracting, in opposite timing, the pistons 136 and 138 of the cylinder pairs 124 and 126 of first and second lifting apparatus 114 and 116.

Figure 16:
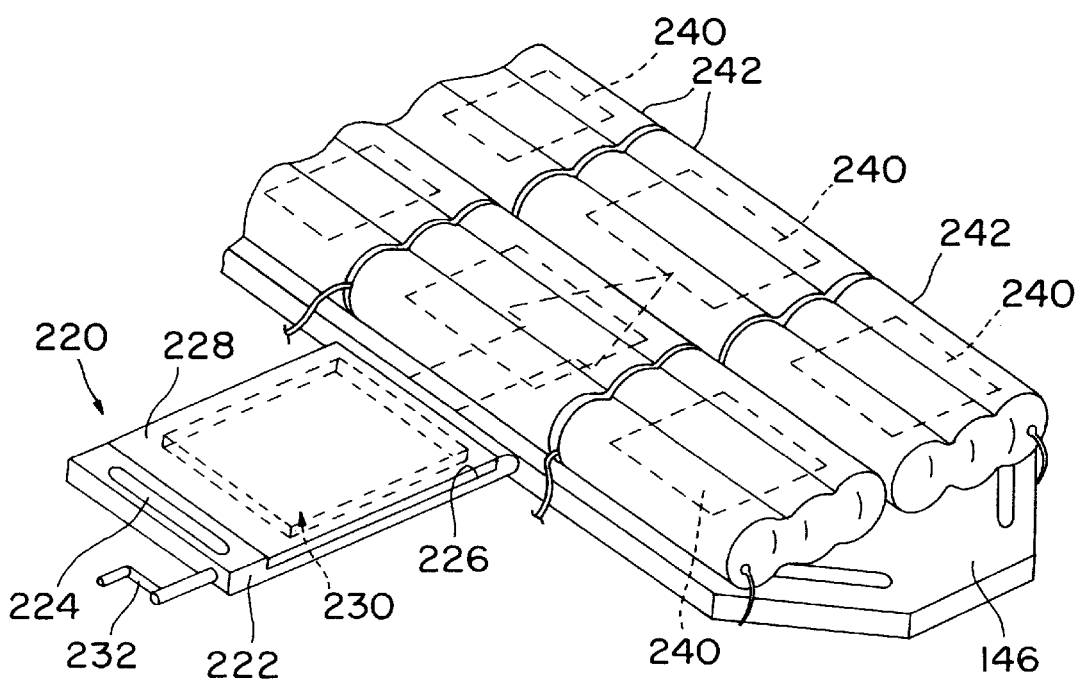
FIG. 16 illustrates insertion of an x-ray cassette below the patient support surface of the present invention.
Figure 17:
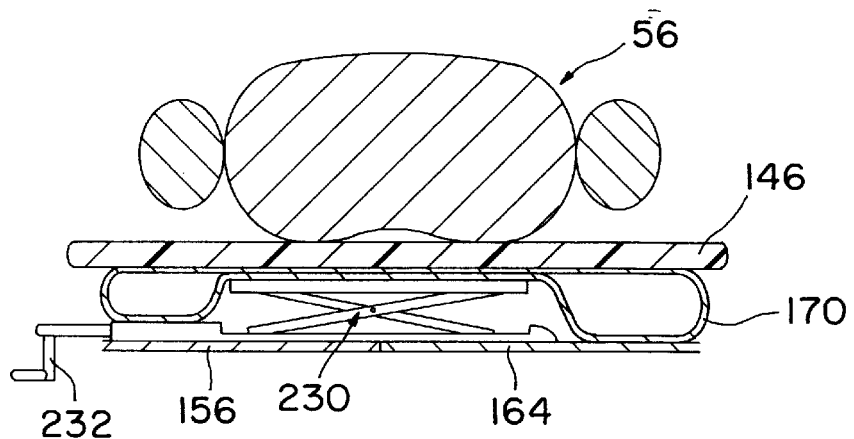
FIG. 17 is a sectional view illustrating actuation of the x-ray cassette holder to move the x-ray cassette close to a patient support surface to improve imaging.

FIGS. 16 and 17 illustrate an x-ray carriage 220 including a frame 222 having a handle 224 and a recessed portion 226 configured to receive an x-ray cassette 228. Carriage 220 also includes a lifting mechanism 230 best illustrated in FIG. 17 which is operated by a crank 232. The carriage 220 is designed to be inserted below bladders 170 and backboard 146 to lie on doors 156 and 164, Appropriate openings (not shown) are formed in door sections 152 or 160 to permit insertion of the carriage 220. Once the carriage 220 is positioned at a desired location, lifting apparatus 230 is actuated to lift the x-ray cassette 228 upwardly as shown in FIG. 17. The bladder 170 above the x-ray cassette 228 is deflated to permit the x-ray cassette 228 to be moved upwardly against a bottom surface of backboard 146. By moving the x-ray cassette 128 closer to the bottom surface of backboard 146, imaging is improved.

In another embodiment of the present invention, the apparatus includes surface pressure sensing integrated into the patient support surface. Specifically, an array of capacitive pressure sensors 240 are coupled to a top surface of patient support bladders 242 as shown in FIG. 16. Foam support surfaces may be located in the air bladders 242, if desired. As a patient 56 changes positions on the support bladders 242, or is rotated within the bed 10, pressure within each bladder 242 is adjusted based on inputs from the pressure sensor array 240 to keep interface pressure below capillary closure pressure or at as low a pressure as possible.

Figure 18:
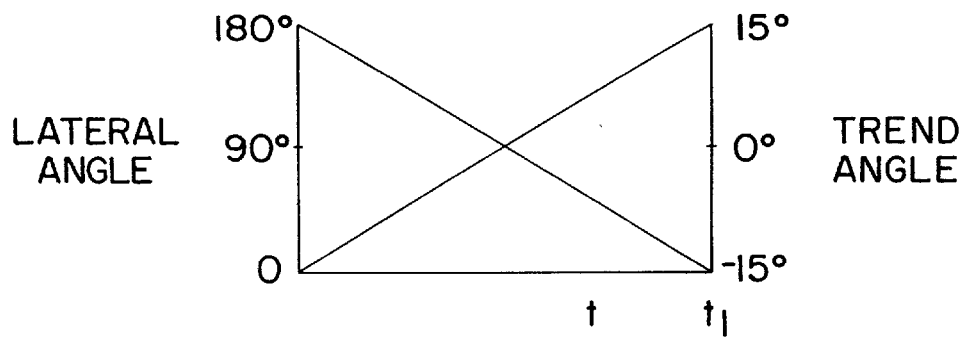
FIG. 18 is a chart illustrating rotation of the patient support surface about both a lateral axis and a longitudinal axis.

As discussed above, the bed of the present invention can be used to provide rotation about longitudinal axis 38 and about a lateral axis generally perpendicular to the longitudinal axis 38. The bed can move the patient about the longitudinal axis 38 up to 360°. At the same time, Trendelenburg angles of +/−15° are also possible. For instance, a patient requiring head elevation and proning can be in reverse Trendelenburg position shown in FIG. 13 while in the supine position. As the patient 56 is rotated to the prone position, the bed also actuates the lifting apparatus or tilting apparatus to move the patient support surface to the Trendelenburg position Therefore, when the patient is in the prone position, the patient's head will still be elevated. A graph shown in FIG. 18 illustrates rotation angles about the lateral axis and longitudinal axis 38.

Figure 19:
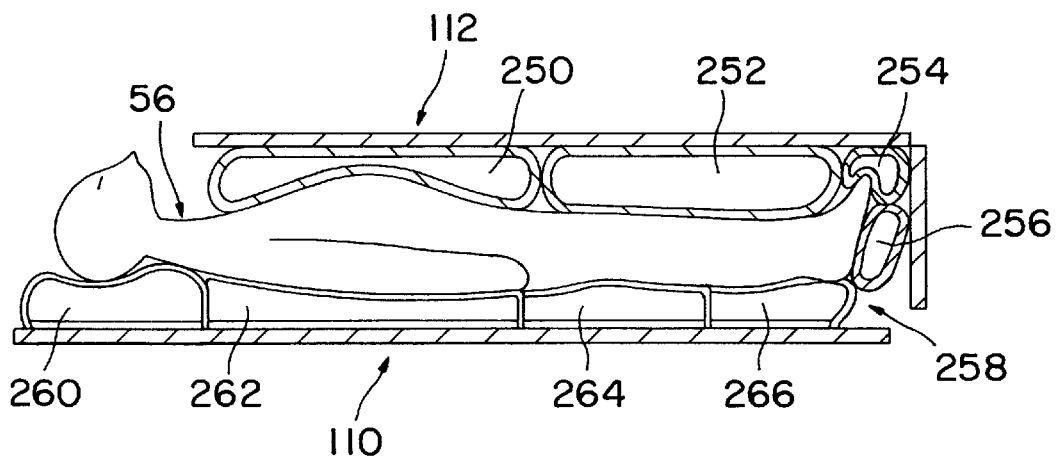
FIG. 19 is a sectional view illustrating a compression therapy apparatus of the present invention.

FIG. 19 illustrates an external chest compression device of the present invention. illustratively, separate air cushions 250, 252, 254, 256 and 258 surround the patient 58 when the proning doors 172 and 174 are closed. The air cushions are all controlled separately. Each air cushion, 250, 252, 254, 256, and 258 may be divided Into separate zones. For instance, zone 258 located below patient 56 may be divided into four separate zones 260, 262, 264 and 266 as indicated, Cushion 250 and a chest and abdomen zone 262 of lower air cushion 258 are increased in pressure to place the patient's chest cavity under varying amounts of external pressure. This may provide respiratory benefits to the patient 56, similar to prone positioning Cushion 250 and chest and abdomen zone 262 of lower air cushion 258 may also be used to provide chest physiotherapy such as percussion or vibration therapy, either separately or together. Inflation and deflation of the cushions may also be synchronized to a patient's breathing pattern and then adjusted to wean the patient from a respirator. Cushions 252, 254, 256 and the leg and foot zones 264 and 266 of bottom cushion 258 are inflated simultaneously to provide deep vein thrombosis therapy. Inflation and deflation of all the zones is controlled by a blower coupled to a main controller of the bed 10. The controller of bed 10 can also be connected to various monitoring outputs from devices such as $SaO_2$, EKG, respiration, etc., and the pressure in the zones can be varied based upon outputs from these monitoring device outputs to synchronize treatment with the physical parameters detected. Interface pressure sensors may be included in each cushion to provide feedback to the controller.

Monitoring devices, such as a patient's blood oxygen level sensor $SaO_2$ monitoring systems are well known. The controller of the present invention is also used to control the frequency of rotation of the patient using feedback from a blood oxygen saturation monitor coupled to the patient. The processor determines whether the patient requires more or less frequent rotation based upon the blood oxygen saturation levels detected and either suggests the change in rotation frequency to the caregiver via a display or automatically adjusts the frequency of rotation of the patient support surface based on the blood oxygen saturation levels detected. The illustrated frequency is about 0.67 degrees per second. This frequency is adjusted based on the output of the blood oxygen saturation monitor.

A controller of the present invention is used to program various features of the bed to provide a sequence of treatments to the patient selected from a matrix of possible bed positions and therapies. The controller can provide continuous lateral rotation of the patient about longitudinal axis 38 at different angles and frequencies. The controller may be programmed to rotate the bed further to one side than to the other during the continuous lateral rotation. In addition, the controller can be programmed to provide head elevation, for example, at selected times. The controller can be coupled to various types of sensors, such as discussed above including sensors for measuring blood oxygen level, oxygen index, end tidialed $CO_2$, etc., to adjust the treatment or position of the patient based on outputs from these sensors.

Although the invention has been described in detail with reference to a certain illustrated embodiment, variations and modifications exist within the scope and spirit of the present invention as described and defined in the following claims.

What is claimed is:

1. A patient support apparatus comprising:
    a base;
    a patient support assembly coupled to the base, the patient support assembly having a patient support surface configured to support a patient; and
    means for simultaneously rotating the patient support assembly about a first axis generally parallel to a longitudinal axis of the patient support assembly, and rotating the patient support assembly about a second axis generally transverse to the longitudinal axis of the patient support assembly alternately in a first direction and a second direction to provide rotational therapy to the patient about both the first and second axes.

2. The apparatus of claim 1, further comprising a frame pivotably coupled to the base about the second axis, the patient support assembly being coupled to the frame, the rotating means including a pivot mechanism coupled between the base and the frame, the pivot mechanism being configured to rotate the frame relative to the base about the second axis to move the support surface from a first generally horizontal position to a selected angled non-horizontal position.

3. The apparatus of claim 1, wherein the rotating means is configured to adjust an angle of the support surface relative to the base between a Trendelenburg position and a reverse Trendelenburg position.

4. The apparatus of claim 1, further comprising a frame coupled to the base, the frame including a rotatable drive mechanism, and the patient support assembly being coupled to the drive mechanism so that the drive mechanism rotates the patient about the first axis.

5. The apparatus of claim 1, further comprising a proning surface configured to be coupled to the patient support assembly, the proning surface being configured to support the patient in a prone position when the patient support assembly is rotated 180° about its longitudinal axis by the rotating means.

6. The apparatus of claim 1, wherein the patient support assembly includes first and second spaced apart arms, and first and second lifting mechanisms coupled to the first and second support arms, respectively, the patient support surface being coupled to the first and second lifting mechanisms, and further comprising a controller coupled to the first and second lifting mechanisms, the controller being configured to actuate the first and second lifting mechanisms to move the patient support surface up and down relative to the first and second support arms.

7. The apparatus of claim 1, wherein the rotating means includes a controller which is programmed to provide a sequence of rotational treatments to the patient.

8. The apparatus of claim 1, further comprising a monitoring device having an output signal indicating a condition of the patient, and a controller coupled to the monitoring device and the rotating means to control rotation of the patient support surface in response to the output signals from the monitoring device.

9. A patient support apparatus comprising;
a base;
a patient support assembly coupled to the base for pivotable movement about a pivot axis generally transverse to a longitudinal axis of the patient support assembly, the patient support assembly having a patient support surface configured to support a patient;
a pivot mechanism coupled to the patient support assembly to rotate the patient support assembly about the pivot axis; and
a controller coupled to the pivot mechanism, the controller being programmable to cause rotation of the patient support assembly about the pivot axis alternately in a first direction and a second direction to provide rotational therapy to the patient.

10. The apparatus of claim 9, wherein the patient support assembly is also pivotable about a second pivot axis generally parallel to the longitudinal axis of the patient support assembly, and further comprising a second pivot mechanism coupled to the patient support assembly to rotate the patient support assembly about the second pivot axis, the controller also being coupled to the second pivot mechanism to control rotation of the patient support assembly about the second pivot axis at a selected rate of rotation and to a selected angle of rotation to provide rotational therapy to the patient.

11. The apparatus of claim 9, wherein the pivot mechanism is configured to adjust a position of the support surface relative to the base between a Trendelenburg position and a reverse Trendelenburg position.

12. The apparatus of claim 9, wherein the patient support assembly includes first and second spaced apart arms, and the pivot mechanism includes first and second lifting mechanisms coupled to the first and second support arms, respectively, the patient support surface being coupled to the first and second lifting mechanisms, the controller being coupled to the first and second lifting mechanisms and configured to actuate the first and second lifting mechanisms to move the patient support surface up and down relative to the first and second support arms to rotate the patient support surface about the pivot axis.

13. The apparatus of claim 9, wherein the controller is programmed to provide a sequence of rotational treatments to the patient.

14. The apparatus of claim 9, further comprising a monitoring device having an output signal indicating a condition of the patient, the controller being coupled to the monitoring device to control rotation of the patient support assembly in response to the output signals from the monitoring device.

15. The apparatus of claim 9, wherein the controller causes the rotation of the patient support assembly according to a predetermined rotational therapy for the patient upon selection of the therapy by a caregiver.

16. The apparatus of claim 9 wherein the controller causes rotation of the patient support assembly about the pivot axis at a selected rate of rotation.

17. The apparatus of claim 9 wherein the controller causes rotation of the patient support assembly about the pivot axis to a selected angle of rotation.

18. A proning apparatus comprising:
a proning device having a first surface configured to be located adjacent a posterior side of the patient to support the patient in a supine position and a proning surface configured to be located adjacent an anterior side of the patient to support the patient in a prone position;
at least one air bladder located on the first surface;
at least one air bladder located on the proning surface; and
a controller configured to alternately inflate and deflate the at least one air bladder located on the first surface and the at least one air bladder located on the proning surface according to a sequence defined by a compression therapy for the patient.

19. The apparatus of claim 18, wherein the at least one air bladder located on the first surface and the at least one air bladder located on the proning surface are located adjacent the patient's chest to provide chest compression therapy the patient.

20. The apparatus of claim 18, wherein a plurality of separately inflatable bladder zones are located on the first surface and the proning surface adjacent at least one of the patient's head, chest, abdomen, legs, and feet.

21. A proning apparatus comprising:
a proning device having a first surface configured to be located adjacent a posterior side of the patient to support the patient in a supine position and a proning surface configured to be located adjacent an anterior side of the patient to support the patient in a prone position;
at least one air bladder located on the first surface;
at least one air bladder located on the proning surface;
a controller configured to selectively inflate and deflate the at least one air bladder located on the first surface and the at least one air bladder located on the proning surface to provide compression therapy to the patient;
a base;
a frame coupled to the base, the frame including a rotatable drive mechanism; and
a patient support assembly coupled to the drive mechanism, the drive mechanism being configured to rotate the patient support assembly at least 180° about its longitudinal axis, the first surface and the proning surface being coupled to the patient support assembly.

22. A proning apparatus comprising:
a proning device having a first surface configured to be located adjacent a posterior side of the patient to support the patient in a supine position and a proning surface configured to be located adjacent an anterior side of the patient to support the patient in a prone position;
at least one air bladder located on the first surface;
at least one air bladder located on the proning surface; and
a controller configured to selectively inflate and deflate the at least one air bladder located on the first surface and the at least one air bladder located on the proning surface to provide compression therapy to the patient;
wherein the controller is programmed to selectively inflate and deflate the at least one air bladder located on the first surface and the at least one air bladder located on the proning surface to provide at least one of chest compression therapy, respiratory therapy, percussion and vibration therapy, and vein thrombosis therapy on the patient.

23. A proning apparatus comprising;
a proning device having a first surface configured to be located adjacent a posterior side of the patient to support the patient in a supine position and a proning surface configured to be located adjacent an anterior side of the patient to support the patient in a prone position;

at least one air bladder located on the first surface;

at least one air bladder located on the proning surface; and a controller configured to selectively inflate and deflate the at least one air bladder located on the first surface and the at least one air bladder located on the proning surface to provide compression therapy to the patient;

wherein the controller is programed to synchronize inflation and deflation of at least one of the air bladders with a breathing pattern of the patient.

24. A patient support apparatus comprising:

a base;

a patient support assembly coupled to the base, the patient support assembly having a patient support surface configured to support a patient;

a first drive mechanism configured to rotate the patient support assembly about a first axis generally parallel to a longitudinal axis of the patient support assembly; and a second drive mechanism configured to rotate the patient support assembly about a second axis generally transverse to the longitudinal axis of the patient support assembly alternately in a first direction and a second direction, while the first drive mechanism rotates the patient support assembly about the first axis to provide rotational therapy to the patient about both the first an second axes.

25. The apparatus of claim 24, further comprising a monitoring device that provides an output signal indicating a condition of the patient, one of the first and the second drive mechanisms being coupled to the monitoring device to change the rotation of the patient support assembly in response to the output signal.

26. The apparatus of claim 24, wherein the first drive mechanism is configured to rotate the patient support assembly at least 180° about the longitudinal axis.

27. The apparatus of claim 24, wherein the first drive mechanism is configured to rotate the patient support assembly to a selectable angular orientation.

28. The apparatus of claim 24, wherein the second drive mechanism is configured to rotate the patient support assembly to a selectable angular orientation.

29. The apparatus of claim 24, wherein the second axis is adjacent an end of the patient support assembly.

30. A patient support apparatus comprising:

a base;

a patient support assembly coupled to the base, the patient support assembly having a patient support surface configured to support a patient; and an electrical controller coupled the patient support assembly to cause simultaneous rotation of the patient support assembly about a first axis generally parallel to a longitudinal axis of the patient support assembly and about a second axis generally transverse to the longitudinal axis of the patient support assembly to provide rotational therapy to the patient about both the first and second axes.

31. The apparatus of claim 30, wherein the controller is programmable.

32. The apparatus of claim 31, wherein the controller automatically causes the simultaneous rotation according to a predetermined rotational therapy for the patient upon selection of the therapy by a caregiver.

33. The apparatus of claim 30, further comprising a monitoring device that provides an output signal indicating a condition of the patient, the electrical controller being coupled to the monitoring device to change the rotation of the patient support assembly in response to the output signal.

34. The apparatus of claim 30, wherein the electrical controller is configured to rotate the patient support assembly at least 180° about the first axis.

35. The apparatus of claim 30, wherein the electrical controller is configured to rotate the patient support assembly to selectable angular orientation.

36. The apparatus of claim 30, wherein the second axis is adjacent an end of the patient support assembly.

37. A method of providing rotational therapy to a patient, including the steps of providing a patient support apparatus having a base and a patient support surface coupled to the base;

positioning the patient on the patient support surface;

alternately rotating the patient support assembly in a first direction and a second direction about a transverse axis generally parallel to a transverse axis of the patient support assembly;

and rotating the patient support assembly about a longitudinal axis generally parallel to a longitudinal axis of the patient support assembly, simultaneous with the alternately rotating step.

38. The method of claim 37, further including the steps of providing a monitoring device to monitor a condition of the patient, and changing the rotation of the patient support assembly in response to an output signal from the monitoring device.

39. The method of claim 37, wherein the step of rotating the patient support assembly about a longitudinal axis includes the step of rotating the patient support assembly at least 180° about the longitudinal axis.

40. The method of claim 37, wherein the step of rotating the patient support assembly about a longitudinal axis includes the step of rotating the patient support assembly to a selectable angular orientation.

41. The method of claim 37, wherein the step of alternately rotating the patient support assembly includes the step of rotating the patient support assembly to a selectable angular orientation.

* * * * *

UNITED STATES PATENT AND TRADEMARK OFFICE
CERTIFICATE OF CORRECTION

PATENT NO.    : 6,499,160 B2
DATED         : December 31, 2002
INVENTOR(S)   : Hand et al.

It is certified that error appears in the above-identified patent and that said Letters Patent is hereby corrected as shown below:

<u>Column 13,</u>
Line 28, please change "first an" to -- first and --.

Signed and Sealed this

Sixteenth Day of December, 2003

JAMES E. ROGAN
*Director of the United States Patent and Trademark Office*